United States Patent

Watanabe et al.

[11] Patent Number: 5,830,339
[45] Date of Patent: Nov. 3, 1998

[54] GAS CONCENTRATION DETECTOR

[75] Inventors: Isao Watanabe; Masahiro Shibata; Tomio Sugiyama, all of Nagoya; Syuichi Nakano; Shinichiro Imamura, both of Kariya, all of Japan

[73] Assignee: Denso Corporation, Kariya, Japan

[21] Appl. No.: 736,911

[22] Filed: Oct. 25, 1996

[30] Foreign Application Priority Data

Oct. 27, 1995 [JP] Japan ................................. 7-303666

[51] Int. Cl.⁶ .............................................. G01N 27/407
[52] U.S. Cl. ........................... 204/426; 204/425; 204/428
[58] Field of Search ............................ 204/421–429

[56] References Cited

U.S. PATENT DOCUMENTS

| | | | |
|---|---|---|---|
| 4,141,813 | 2/1979 | Kita et al. | 204/428 |
| 4,158,827 | 6/1979 | Maurer et al. | 204/428 |
| 4,219,399 | 8/1980 | Gruner et al. | 204/428 |
| 4,225,634 | 9/1980 | Tanaka et al. | 204/428 |
| 4,370,213 | 1/1983 | Oki et al. | 204/428 |
| 4,502,939 | 3/1985 | Holfelder et al. | 204/428 |
| 4,505,807 | 3/1985 | Yamada | 204/426 |
| 4,597,850 | 7/1986 | Takahashi et al. | 204/426 |
| 4,980,044 | 12/1990 | Ker . | |
| 5,518,603 | 5/1996 | Furuhashi et al. | 204/426 |

FOREIGN PATENT DOCUMENTS

| | | |
|---|---|---|
| 63-11644 | 4/1983 | Japan . |
| 60-033046 | 2/1985 | Japan . |
| 6-029877 | 4/1994 | Japan . |

*Primary Examiner*—T. Tung
*Attorney, Agent, or Firm*—Cushman Darby & Cushman IP Group of Pillsbury Madison & Sutro LLP

[57] ABSTRACT

A gas concentration detector comprises a plate sensor element including a sensing action and a signal output section. A flange section is formed between the sensing section and the signal output section so as to protrude in the lateral direction thereof. A cylindrical housing has an inside space for receiving the sensor element. Powder is disposed in the inside space of the cylindrical housing at a predetermined position adjacent to the flange section so that the sensor element is airtightly fixed to the housing by applying a pressing force on the powder. Furthermore, a cross-sectional area of the signal output section is larger than a cross-sectional area of the sensing section.

19 Claims, 5 Drawing Sheets

GAS CONCENTRATION DETECTOR

BACKGROUND OF THE INVENTION

1. Field of the Invention

This invention relates to a gas concentration detector, such as an air-fuel ratio sensor used in the air-fuel ratio control of an internal combustion engine for an automotive vehicle.

2. Related Art

Figure 13:
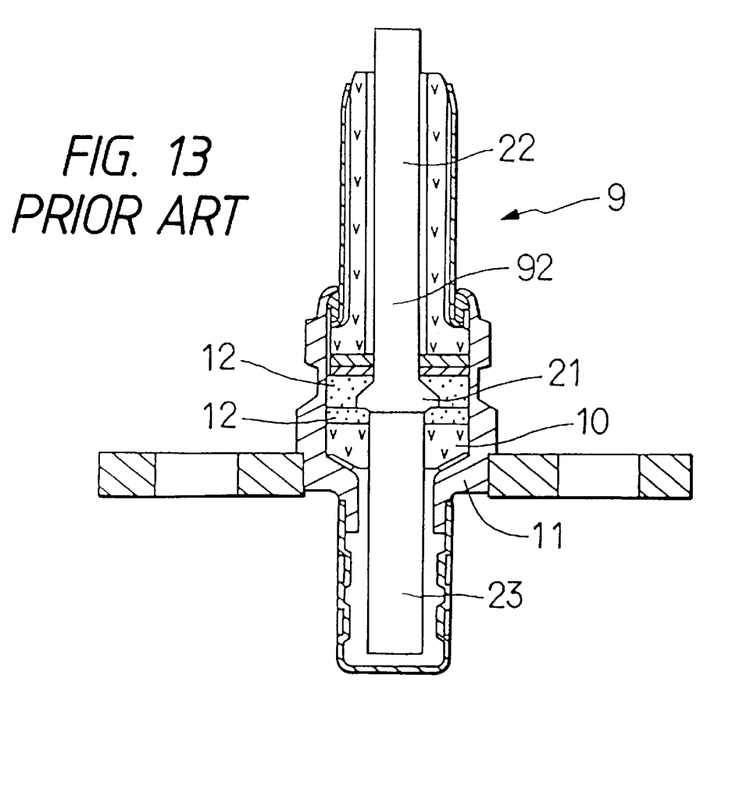
FIG. 13 is a cross-sectional view showing a conventional air-fuel ratio sensor.

In an advanced internal combustion engine for an automotive vehicle, an air-fuel ratio sensor is provided in an exhaust passage of the engine for air-fuel ratio control. FIG. 13 shows one example of such an air-fuel ratio sensor.

In FIG. 13, an air-fuel ratio sensor 9 comprises an elongated plate-like (i.e. rectangular) sensing section 23 and an elongated plate-like (i.e. rectangular) signal output section 22. A flange section 21 is formed between these rectangular sensing section 23 and signal output section 22 so as to protrude from the side of these sections 22 and 23 in the lateral direction of air-fuel ratio sensor 9. These sections 21 through 23 cooperatively constitute an elongated plate-like (i.e. rectangular) sensor element 92, which is inserted into an inside space of a cylindrical housing 11 and supported by a holder 10. Powder 12 is provided at a predetermined position above the holder 10.

Powder 12 is then compressed by receiving a pressing force applied in the up-and-down direction, so that sensor element 92 is air-tightly fixed to the inside of the holder 10 and housing 11 (For more details, refer to Japanese Utility Model No. SHO 63-11644, published in 1988). An inside space, defined by upper and lower surfaces of flange section 21, a side surface of sensor element 92 and an inside surface of housing 11 in the vicinity of flange section 21, serves as an accommodation space for receiving or storing powder 12.

However, the above-described conventional air-fuel ratio sensor has the following problems.

The sensor element used in the above-described conventional air-fuel ratio is rectangular in shape. Therefore, compared with a cup-shaped (i.e. circular) sensor element, the cross-sectional area of the powder-accommodation space tends to become large. It means that, in the pressing operation of fixing the sensor element air-tightly to the inside of the housing by applying a force on the powder, a pressing force required for this rectangular sensor element will become significantly large compared with a pressing force required for the circular sensor element.

More specifically, the rectangular sensor element necessarily enlarges the cross-sectional area of the powder-accommodation space compared with the circular sensor element. This fact brings the definite relationship that the substantial pressing force per unit area becomes smaller and insufficient when the sensor element is a rectangular shape, compared with the circular sensor element, when the pressing force applied on the powder is identical in both cases. Reduction of the pressing force will directly cause the lack of condensation of the powder. In other words, there is the possibility that the sensor element may not be air-tightly fixed to the inside space of the sensor housing.

Moreover, such an insufficient density of the powder will possibly lead to application of an excessively large force on the powder to acquire satisfactory powder density; thus, the sensor element may possibly be cracked or damaged due to its fragility.

Furthermore, the above-described pressing force is obtained from a caulking force applied to the upper end of the housing to fix a cover, such as an atmosphere-side cover, located at the upper end of the housing. Hence, increasing this pressing force is equal to performing the caulking operation by an increased force. This will raise another problem of the reliability in the strength of the portion to be caulked.

According to the plate-like sensor element shown in the Japanese Utility Model No. SHO 63-11644, the cross-sectional area of the sensing section 23 is larger than that of the signal output section 22. From this relation, it is inevitable that the cross-sectional area of the powder-accommodating space is further enlarged. It means that the pressing force applied on the powder needs to be further increased.

Still further, the above-described conventional sensor element has a large heat capacity due to the large cross-sectional area of the sensing section 23. Accordingly, the above-described conventional sensor element cannot increase its temperature so quickly. In other words, it takes a significantly long time, after the engine is started up, until the temperature of the sensor element is increased to a predetermined high temperature required for effecting the air-fuel ratio detecting function. In this case, it is needless to say that the exhaust gas purification efficiency is worsened in this elongated warming-up duration.

Yet further, according to the above-described conventional sensor element, the size (i.e. cross-sectional area) of the signal output section becomes smaller. This is inconvenient and disadvantageous for the sensor element having numerous lead lines, such as a later-described 2-cell type (see FIG. 8) sensor element, because a relatively small and insufficient surface of the signal output section is available for the portion for arranging or disposing the lead lines. It is needless to say that narrowly arranging the lead lines will cause the short-circuit problem.

The above-described problems will be solved more or less if the sensor element has a sensing section and a signal output section having the identical configuration.

However, this kind of symmetric sensor element has the drawback in that it is difficult to discriminate between the sensing section and the signal output section. Hence, in assembling these air-fuel ratio sensors, the sensor element may be accidentally installed upside down.

SUMMARY OF THE INVENTION

Accordingly, in view of above-described problems encountered in the related art, a principal object of the present invention is to provide a gas concentration detector which has an excellent sealing ability between a sensor element and a housing, and is capable of quickly increasing the temperature of the sensor element, and further prevents any erroneous installation of the sensor element into the housing, and yet further eliminates the short-circuit problem even when numerous lead lines are provided for enhancing the sensor performance.

In order to accomplish this and other related objects, the present invention provides a gas concentration detector comprising a plate-like sensor element including an elongated plate-like sensing section, an elongated plate-like signal output section, and a flange section disposed between the sensing section and the signal output section so as to protrude in a lateral direction. A cylindrical housing of this gas concentration detector has an inside space for receiving the sensor element. And, powder is disposed in the inside space of the cylindrical housing at a predetermined position above the flange section of the plate-like sensor element, so that the sensor element is air-tightly fixed to the housing by applying a pressing force on the powder. As the characteristic features of the present invention, a cross-sectional area of the signal output section is larger than a cross-sectional area of the sensing section, when the cross-sectional area is defined by each outer periphery of the signal output section and the sensing section along a plane normal to the axis of the sensor element.

According to features of the preferred embodiments of the present invention, the flange section has upper and lower surfaces, and at least one of the upper and lower surfaces is tapered. The cylindrical housing has an inclined support surface on an inside surface thereof, and the flange section has a tapered portion supported by the inclined support surface, so that the flange section is brought into contact with the inclined support surface along an outermost periphery of the tapered portion.

Furthermore, it is preferable that a washer is interposed between the cylindrical housing and the sensor element. The sensor element may comprise a plate-like solid electrolyte made of oxygen ion conductive metallic oxide, and a pair of electrodes provided on this solid electrolyte. Yet further, the sensor element may comprise a sensor section comprising a pair of electrodes provided on a plate-like solid electrolyte made of oxygen ion conductive metallic oxide, and the solid electrolyte is bonded on a substrate made of electrical insulating metallic oxide. Preferably, the substrate made of electrical insulating metallic oxide has the flange sections protruding in the lateral direction, while the solid electrolyte has no flange.

Yet further, the sensor element may be a two-cell type sensor element comprising a pump cell and a sensor cell which are stacked. And, it will be preferable that the sensor element comprises a heater element.

BRIEF DESCRIPTION OF THE DRAWINGS

The above and other objects, features and advantages of the present invention will become more apparent from the following detailed description which is to be read in conjunction with the accompanying drawings, in which.

DETAILED DESCRIPTION OF THE PREFERRED EMBODIMENTS

Preferred embodiments of the present invention will be explained in greater detail hereinafter with reference to the accompanying drawings. Identical parts are denoted by the same reference numerals throughout the views.

Embodiment 1

A gas concentration detector in accordance with the first embodiment of the present invention will be explained with reference to FIGS. 1 through 5. The gas concentration detector of the present invention can be preferably used for detecting the concentration of $O_2$, $NO_x$, HC and other gases.

Figure 1:
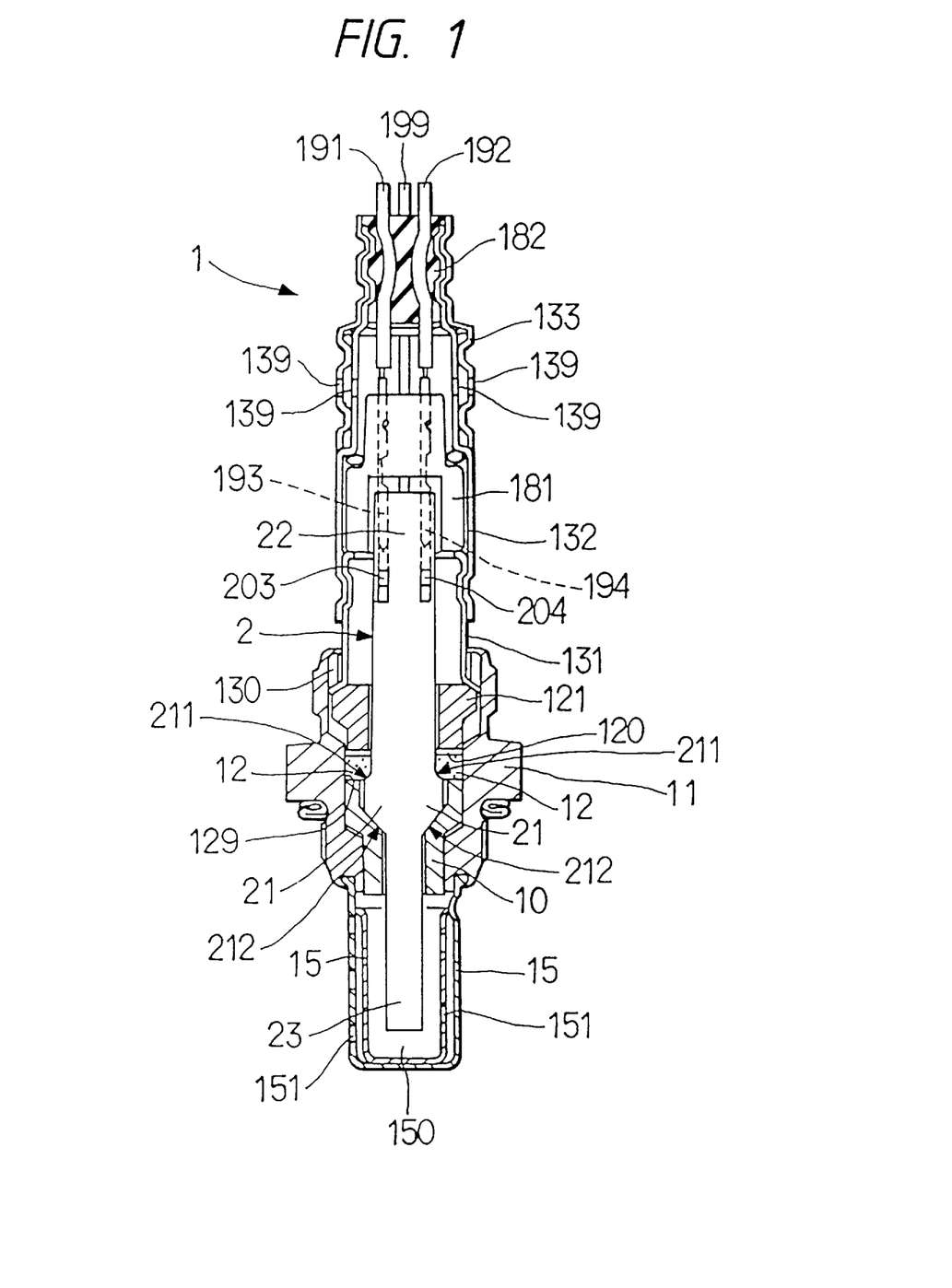
FIG. 1 is a cross-sectional view showing a gas concentration detector in accordance with a first embodiment of the present invention.

As shown in FIG. 1, a gas concentration detector 1 comprises an elongated plate-like sensing section 23 having a rectangular (or quadrangular or polygonal) cross section and an elongated plate-like signal output section 22 having a rectangular (or quadrangular or polygonal) cross section. A flange section 21 is formed between these rectangular sensing section 23 and signal output section 22 so as to protrude from the side of these sections 22 and 23 in the lateral direction of gas concentration detector 1 (or sensor element 2). These sections 21 through 23 are integrally formed and cooperatively constitute an elongated plate-like (e.g. rectangular) sensor element 2, which is inserted into an inside space of a cylindrical housing 11. Powder 12 is provided above the flange section 21.

Powder 12 is then compressed by receiving a pressing force applied in the up-and-down direction, so that sensor element 2 is air-tightly fixed to the inside space of housing 11.

According to the sensor element 2 of this first embodiment, the signal output section 22 has a cross-sectional area larger than that of sensing section 23. In this embodiment, each cross-sectional area of signal output section 22 and sensing section 23 is defined by an outer periphery of each member along a plane normal to the axis of the gas concentration detector 1 (or sensor element 2).

Hereinafter, the arrangement of gas concentration detector 1 in accordance with the first embodiment will be explained in greater detail.

Gas concentration detector 1 comprises a double-wall cover 15 which is disposed under the housing 11 and subjected to the gas to be sensed, as well as three-story covers 131, 132 and 133 which are disposed above the housing 11 and are sequentially or successively arranged to be exposed to the atmosphere (i.e. air). A gas chamber 150, sensing the concentration of gas to be detected, is defined by the inside wall of double-wall cover 15 and the lower end of housing 11. A plurality of gas holes 151 are formed on the double-wall cover 15 to introduce the gas into gas chamber 150.

The lowermost cover 131, disposed at the lowest position of the sequential three-story covers in the atmosphere side, is fixed to housing 11 through ring 130 by caulking. The intermediate cover 132 is fixed on the lowermost cover 131 by caulking, and the uppermost cover 133 is fixed on the intermediate cover 132. The force caused through this caulking fixation is transmitted to powder 12 via the lower end of cover 131, an insulator 121 and a packing 120 later described. This force acts on powder 12 as a pressing force applied thereon.

The intermediate and uppermost covers 132 and 133 have inlet openings 139 introducing air into an atmospheric chamber 250 (later-described) provided inside the sensor element 2.

Sensor element 2 is inserted in the inside space of housing 11 and fixedly supported by a holder 10. An accommodation chamber 129 for accommodating powder 12 is defined by a space, enclosed by the holder 10, an upper surface 211 of the flange section 21 of sensor element 2, and the inside surface of housing 11. Packing 120 and insulator 121 are mounted on powder 12. The upper surface of insulator 121 is brought into contact with the lowermost cover 131.

Reference numerals 181 and 182 represent an insulator and a rubber bush, respectively, which cooperatively connect output terminals 193, 194 to output leads 191 and 192 while keeping them in an insulated condition.

Next, details of sensor element 2 will be explained.

Figure 2:
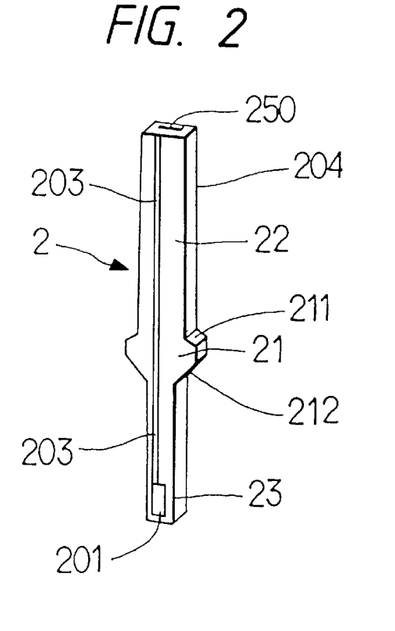
FIG. 2 is a perspective view showing a sensor element incorporated in the gas concentration detector in accordance with the first embodiment of the present invention.

As shown in FIG. 2, the flange section 21 of sensor element 2 has upper and lower surfaces 211 and 212 which are both tapered surfaces.

Figure 3:
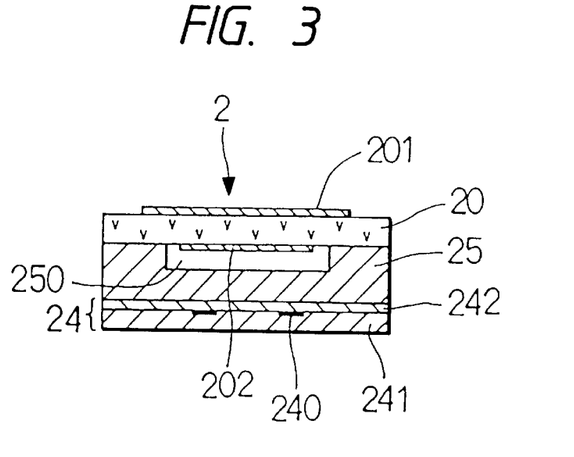
FIG. 3 is a cross-sectional view showing the sensor element incorporated in the gas concentration detector in accordance with the first embodiment of the present invention.

As shown in FIG. 3, sensor element 2 comprises a pair of electrodes 201 and 202 provided on opposite flush surfaces of a plate-like solid electrolyte 20 made of oxygen ion conductive metallic oxide. Solid electrolyte 20 is made of zirconia. Electrodes 201 and 202 are made of platinum and constitute a sensor section which is provided on a flush surface of sensor element 2 on which no flange portion is formed, as shown in FIG. 2. Electrode 201 is exposed in the gas chamber 150 (see FIG. 1), while electrode 202 is exposed to the atmospheric chamber 250 provided inside the sensor element 2.

As shown in FIG. 3, atmospheric chamber 250 is defined by the above-described flat solid electrolyte 20 bonded with an atmospheric-chamber forming plate 25 having a U-shaped groove and being made of alumina.

Sensor element 2 comprises a heater section 24 bonded to the other side of atmospheric-chamber forming plate 25 so as to be opposed to the atmospheric chamber 250. This heater section 24 comprises a substrate 242 with a heater element 240 printed thereon and an insulation plate 241 disposed to cover the heater element 240.

Substrate 242 and insulation plate 241 are made of electrical insulating metallic oxide such as alumina. Heater element 240 is made of tungsten.

Electrodes 201 and 202 of sensor element 2 are integrally connected to lead section 203 and 204, respectively, for taking out detection signals. As shown in FIG. 1, lead section 203 is connected to lead 191 via output terminal 193. In the same manner, lead section 204 is connected to lead line 192 via output terminal 194.

Furthermore, the heater element 240 has a lead section which receives electric power supplied from an external power source. More specifically, this lead section is connected to a current-supply line 199 elongated from an electric power source (refer to FIG. 1).

Next, the function and effect of the first embodiment will be explained.

Figure 4:
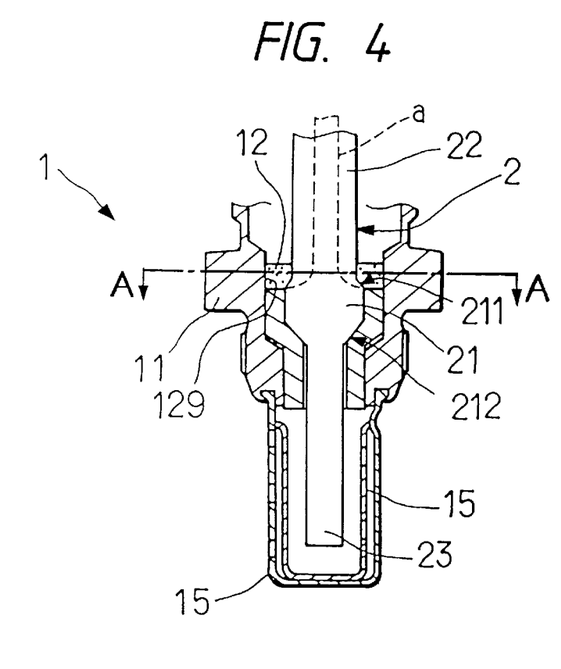
FIG. 4 is a cross-sectional view showing an essential part of the gas concentration detector in accordance with the first embodiment of the present invention.

The sensor element 2 of gas concentration sensor 1 in accordance with the first embodiment, as shown in FIG. 4, has the signal output section 22 having the cross-section area larger than that of sensing section 23. The sensor element 2 is air-tightly fixed in the inside space of holder 10 and housing 11, by filling and press fitting the powder 12 in the accommodation chamber 129 enclosed by housing 11, flange section 21, the side surface of sensor element 2, holder 10, at the position above the flange section 21 of the sensor element 2.

Figure 5:
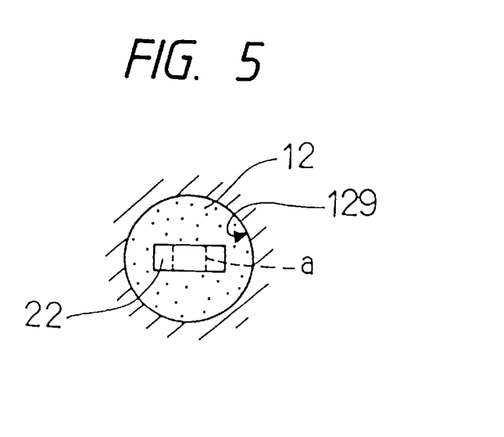
FIG. 5 is a cross-sectional view taken along a line A—A of FIG. 4.

Accordingly, as shown in FIGS. 4 and 5, the cross-sectional area of accommodation chamber 129 along the outer periphery thereof decreases in proportion to the cross-sectional area of signal output section 22 of sensor element 2. For example, if an imaginory signal output section indicated by a dotted line "a" in FIGS. 4 and 5 is inserted and disposed in the housing, the cross-sectional area of the accommodation chamber 129 will become larger than that of the above-described embodiment.

The force acting on powder 12 per unit area increases with reducing cross-sectional area of accommodation chamber 129. Hence, it becomes possible to obtain a satisfactory density of powder 12 even if the pressing force acting on the powder 12 is small. Accordingly, the sealing ability between sensor element 2 and holder 10 or housing 11 can be increased.

Furthermore, according to the above-described sensor element 2, the size of sensing section 23 is relatively small. Hence, sensing section 23 has a small heat capacity, and hence the temperature of sensor element 2 can increase quickly. Accordingly, when the to-be-detected gas has a lower temperature, the sensor element 2 needs to be warmed up by heater section 24 equipped therein to increase the temperature to a predetermined active level. In such a case, the arrangement of the first embodiment makes it possible to shorten the warm-up time due to its small heat capacity.

Furthermore, according to the above-described sensor 2, the configuration of signal output section 22 is different from that of sensing section 23. Hence, the erroneous installation of sensor element 2 into the housing 11 can be surely prevented.

Yet further, flange section 21 has the tapered upper surface 211. With this arrangement, flange section 21 can be brought into contact with powder 12 at an increased area. Accordingly, the stress per unit area acting from powder 12 to flange section 21 can be reduced.

Still further, flange section 21 has the tapered lower surface 212. With this arrangement, flange section 21 can be brought into contact with holder 10 at an increased area. Accordingly, the stress per unit area acting from holder 10 to flange section 21 can be reduced.

As explained above, the overall stress acting on flange section 21 can be effectively reduced, and it becomes possible to prevent flange section 21 from being damaged. Furthermore, it becomes possible to prevent the sensor element 2 from being broken at or in the vicinity of flange section 21.

Moreover, according to the gas concentration detector 1 in accordance with the first embodiment, the cross-sectional area of signal output section 22 of sensor element 2 is relatively large. This is advantageous in that output terminals 193 and 194 of electrodes 201 and 202 or wiring of heater element 240 can be easily disposed or installed on signal output section 22. Short-circuit problem between wires can be surely prevented.

Embodiment 2

Figure 6:
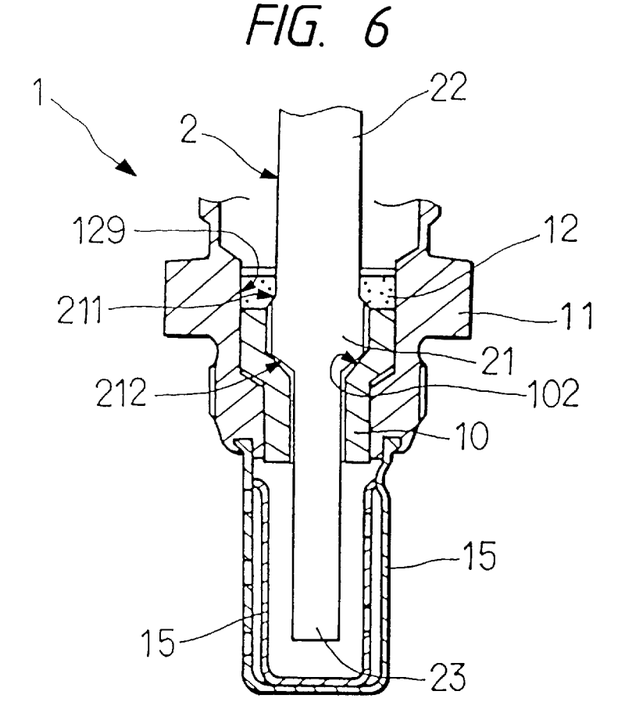
FIG. 6 is a cross-sectional view showing an essential part of a gas concentration detector in accordance with a second embodiment of the present invention.
Figure 7:
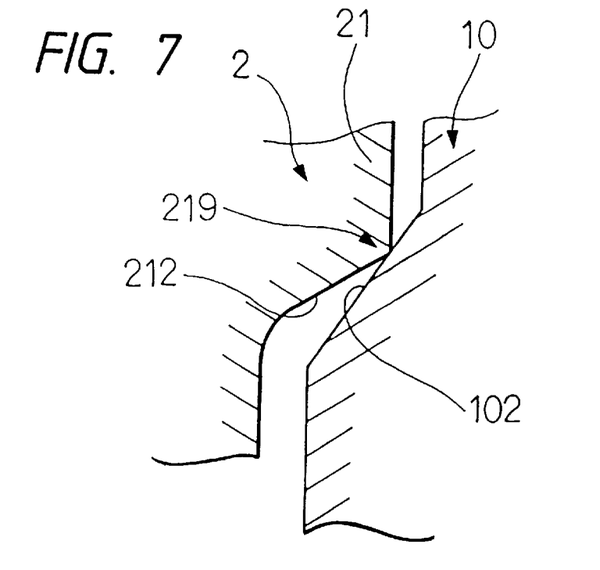
FIG. 7 is a cross-sectional view enlargedly showing the engagement between a sensor element and a holder in accordance with the second embodiment of the present invention.

According to a second embodiment of the present invention, sensor element 2 is inserted in the inside space of housing 11 and fixedly supported by holder 10, as shown in FIGS. 6 and 7. The gas concentration detector 1 in accordance with the second embodiment is characterized in that sensor element 2 is brought into contact with an inclined support surface 102 of holder 10 at the tapered portion of its flange section 21 along an outermost peripheral portion 219.

It is possible to form the outer peripheral portion 219 into a round surface. It is also possible to provide a metallic washer between sensor element 2 and holder 10. Furthermore, it is possible to remove the holder 10 so that the flange section 21 of sensor element 2 can be directly brought into contact with the housing 11.

According to the gas concentration detector 1, sensor element 2 identical with that of the above-described first embodiment is inserted and fixedly supported in the cylindrical housing 11 through holder 10. Powder 12 is provided or disposed at a predetermined position above the flange section 21. Powder 12 is then compressed by receiving a pressing force applied in the up-and-down direction, so that sensor element 2 is air-tightly fixed to the inside of holder 10 and housing 11.

Holder 10 comprises the inclined support surface 102 formed on the inside surface thereof. Furthermore, the lower surface 212 of flange section 21 has a tapered portion supported by the above-described inclined support surface 102.

As shown in FIG. 7, the flange section 21 can be brought into contact with the inclined support surface 102 along the outermost peripheral portion 219 which is part of the tapered portion. Other configuration is substantially the same as that of the first embodiment.

With the arrangement of the second embodiment, the stress acting from the inclined support surface 102 is received by the outer portion of flange section 21 having a larger diameter. Accordingly, the stress per unit area can be decreased in the inside of flange section 21 to a level capable of preventing the damage of flange section 21. The function and effect of the first embodiment can be obtained in this second embodiment in the same manner.

Embodiment 3

Figure 8:
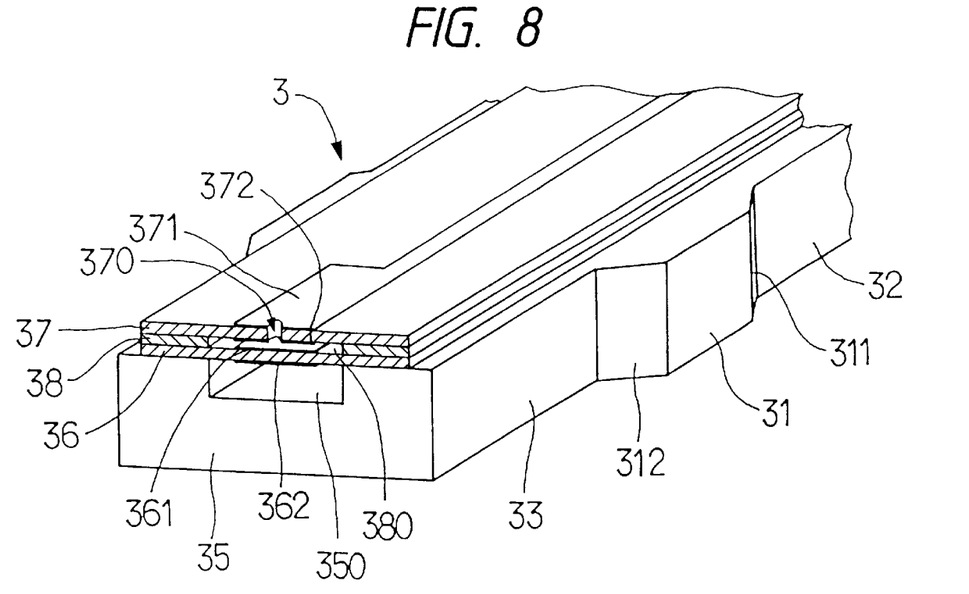
FIG. 8 is a cross-sectional view showing a 2-cell type sensor element in accordance with a third embodiment of the present invention.

A gas concentration detector in accordance with the third embodiment of the present invention is characterized in that, as shown in FIG. 8, there is provided a two-cell type sensor element 3 comprising an elongated plate-like (e.g. rectangular) sensing section 33, an elongated plate-like (e.g. rectangular) signal output section 32, and a flange section 31 formed between these rectangular sensing section 33 and signal output section 32 so as to protrude from the side of these sections 22 and 23 in the lateral direction of sensor element 3. Sensor element 3 is inserted and fixedly held in the housing of the gas concentration detector in the same manner as in the first embodiment.

According to the sensor element 3 of the third embodiment, the signal output section 32 has a cross-sectional area larger than that of sensing section 33. In this embodiment, each cross-sectional area of signal output section 32 and sensing section 33 is defined by an outer periphery of each member along a plane normal to the axis of the gas concentration detector 1 (or sensor element 3). The flange section 31 has an upper surface 311 and a lower surface 312 which are both tapered.

Sensor element 3 comprises a pump cell 37, a sensor cell 36, an inside chamber 380 defined between these cells 36 and 37 to introduce the gas to be sensed, and an atmospheric chamber 350 facing to sensor cell 36 to introduce air therethrough.

The pump cell 27 comprises a pair of electrodes 371 and 372. A pin hole 370 is opened at the center of each of these electrodes 371 and 372. Similarly, the sensor cell 36 has a pair of electrodes 361 and 362.

In the drawing, reference numerals 38 and 35 represent plate components used for forming the inside chamber 380 and the atmospheric chamber 350. Other configuration is the same as that of the first embodiment.

The sensor element 3 shown in this third embodiment comprises a total of four electrodes. Hence, it is necessary to provide four lead lines connected to these electrodes on the signal output section 32. However, according to the sensor element 3 of the third embodiment, the signal output section 32 is relatively large. It means that the lead lines can be easily connected or installed while keeping an adequate gap therebetween without causing the short-circuit problem. The function and effect of the first embodiment can be obtained in the same manner in this third embodiment.

The lead line connected to sensor cell 36 is used for sending out the detection signal from sensor cell 36, while the lead line connected to pump cell 37 is used for applying an electric voltage to pump cell 37.

Embodiment 4

Figure 9:
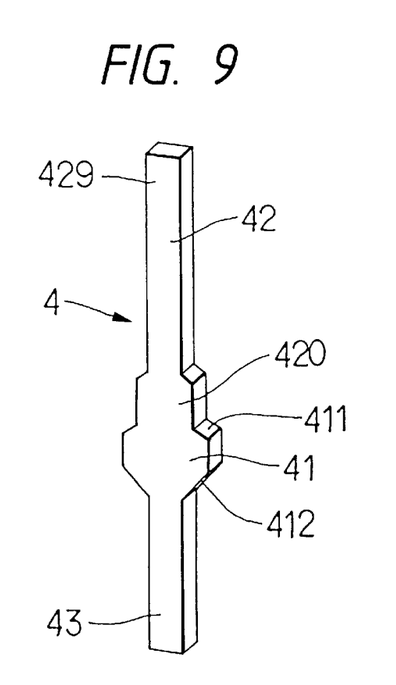
FIG. 9 is a perspective view showing a sensor element in accordance with a fourth embodiment of the present invention.

A sensor element 4 in accordance with the fourth embodiment of the present invention is characterized in that as shown in FIG. 9 the cross-sectional area of a signal output section 42 is differentiated along the longitudinal (up-and-down) direction thereof. Sensor element 4 of the fourth embodiment is inserted and fixedly supported in the same manner as in the first embodiment.

The sensor element 4 comprises an elongated plate-like (e.g. rectangular) sensing section 43, the elongated plate-like (e.g. rectangular) signal output section 42, and a flange section 41 provided therebetween so as to protrude from the side thereof.

The cross-sectional area of a lower part 420 of signal output section 42 is larger than the cross-sectional area of sensing section 43. The lower part 420 is located just above the flange section 41.

The cross-sectional area of an upper part 429 of signal output section 42 is substantially the same as that of sensing section 43. Other configuration is the same as the first embodiment.

In the installation of the sensor element 4 of this fourth embodiment into the housing of the gas concentration detector, a sufficient amount of powder is provided and press fitted into a predetermined space above the flange 41 in the same manner as in the first embodiment. The cross-sectional area of the lower part 420 of signal output section 42 is relatively large; therefore, the cross-sectional area of the powder accommodation chamber can be reduced. Accordingly, the force acting on the powder per unit area is increased, so that the powder density can be satisfactorily obtained. Hence, it becomes possible to provide an excellent sealing ability between sensor element 4 and the housing. The function and effect of the first embodiment can be obtained in this fourth embodiment, too.

Embodiment 5

Figure 10:
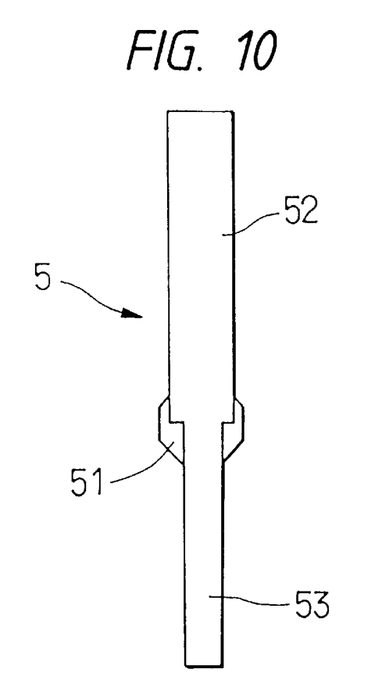
FIG. 10 is a view illustrating a sensor element in accordance with a fifth embodiment of the present invention.
Figure 11:
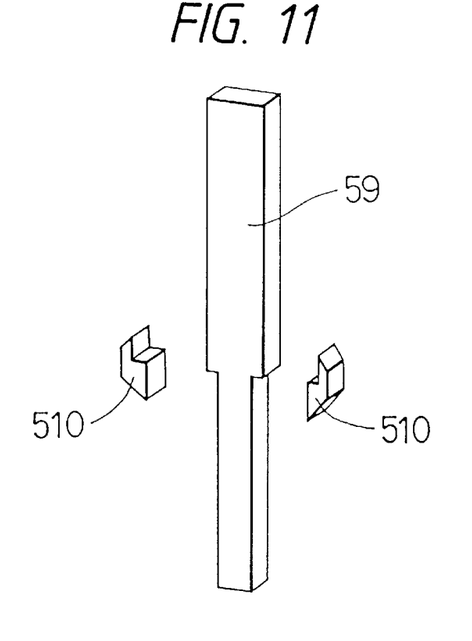
FIG. 11 is a view illustrating the development of the sensor element in accordance with the fifth embodiment of the present invention.
Figure 12:
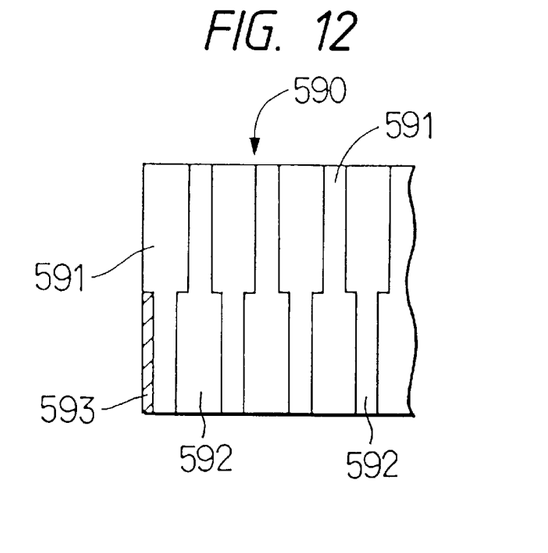
FIG. 12 is a view illustrating a method of forming solid electrolyte in accordance with the fifth embodiment of the present invention.

A sensor element 5 in accordance with the fifth embodiment of the present invention is characterized in that, as shown in FIGS. 10 through 12, a flange section 51 is independently or separately formed.

The sensor element 5 of the fifth embodiment comprises an elongated plate-like (e.g. rectangular) sensing section 53, an elongated plate-like (e.g. rectangular) signal output section 52, and the flange section 51 formed therebetween so as to protrude from the side thereof.

The cross-sectional area of signal output section 52 is larger than the cross-sectional area of sensing section 53.

Furthermore, sensor element 5 comprises a solid electrolyte having a pair of electrodes, an atmospheric-chamber forming plate for defining an atmospheric chamber, and a heater section. The detailed configuration of this sensor element is substantially identical with that of sensor element 2 of the first embodiment shown in FIG. 3. The heater section is constituted by a substrate with a heater element and an insulation plate covering this substrate.

The sensor element 5 of the fifth embodiment is manufactured by connecting or bonding the separate-type flange section to the sensor main body.

First of all, an elongated green sheet 590 made of oxygen ion conductive material is prepared. Next, as shown in FIG. 12, numerous solid electrolytes 591 and 592 having the same shape but disposed upside down are cut or rapped out from this green sheet 590. In this case, solid electrolytes 591 and 592 are alternately arranged so that the smallest amount of waste 593 is formed only at the edge of green sheet 590.

Next, according to the above-described method, the atmospheric-chamber forming plate, the insulation plate, and the substrate are successively produced from the green sheet made of alumina. The atmospheric-chamber forming plate has a surface on which a groove is provided to define the atmospheric chamber when it is assembled with other members.

Next, electrodes are printed on opposite surfaces of the solid electrolyte. Furthermore, a heat element is printed on one surface of the substrate.

Subsequently, the solid electrolyte, atmospheric chamber, insulation plate, and substrate are successively stacked or accumulated to constitute an assembly body 59. The arrangement of assembly body 59 is substantially the same as that shown in FIG. 3.

On the other hand, small pieces 510 and 510 having the same configuration as the above-described flange section 51 are manufactured from alumina by the injection molding.

Then, as shown in FIG. 11, a pair of small pieces 510 and 510 are bonded to the right and left sides of the assembly body 59 by using ceramic adhesive.

The assembly body 59 and associated small pieces 510 and 510, manufactured according to the above-described manufacturing method, are then applied heat to sinter and integrate them into the sensor element 5.

According to the manufacturing method of the sensor element 5 of the fifth embodiment, the amount of waste can be reduced in the process of cutting or rapping out the solid electrolytes from the green sheet. It is advantageous in the saving of material and reduction of manufacturing costs.

As this invention may be embodied in several forms without departing from the spirit of essential characteristics thereof, the present embodiments described are therefore intended to be only illustrative and not restrictive, since the scope of the invention is defined by the appended claims rather than by the description preceding them, and all changes that fall within the metes and bounds of the claims, or equivalents of such metes and bounds, are therefore intended to be embraced by the claims.

What is claimed is:

1. A gas concentration detector comprising:
   a plate sensor element including a sensing section, an elongated signal output section, and a flange section positioned between said sensing section and said signal output section, said flange section being formed by a protruding side face of said plate sensor element;
   a cylindrical housing having an inside space for receiving said plate sensor element; and
   powder disposed in said inside space of said cylindrical housing at a predetermined position adjacent to said flange section of said sensor element, so that said sensor element is surrounded by said powder in an air tight fashion along an entire periphery thereof and fixed to said housing by applying a pressing force on said powder, wherein
   a cross-sectional area of said signal output section is larger than a cross-sectional area of said sensing section, when the cross-sectional area is defined by each outer periphery of said signal output section and said sensing section taken along a plane normal to a longitudinal axis of said sensor element,
   said flange section is provided at only a portion of said entire periphery of said plate sensor, and
   said flange section is supported by said cylindrical housing with no intervening powder.

2. The gas concentration detector in accordance with claim 1, wherein said flange section has upper and lower surfaces, and at least one of said upper and lower surfaces is tapered.

3. The gas concentration detector in accordance with claim 1, wherein said cylindrical housing has an inclined support surface on an inside surface thereof, and said flange section has a tapered portion supported by said inclined support surface, so that said flange section is brought into contact with said inclined support surface along an outermost periphery of said tapered portion.

4. The gas concentration detector in accordance with claim 1, wherein a washer is interposed between said cylindrical housing and said sensor element.

5. The gas concentration detector in accordance with claim 1, wherein said sensor element comprises a plate solid electrolyte made of oxygen ion conductive metallic oxide, and a pair of electrodes provided on said solid electrolyte.

6. The gas concentration detector in accordance with claim 1, wherein said sensor element comprises a sensor section comprising a pair of electrodes provided on a plate solid electrolyte made of oxygen ion conductive metallic oxide, and said solid electrolyte is bonded on a substrate made of electrical insulating metallic oxide.

7. The gas concentration detector in accordance with claim 6, wherein said substrate made of electrical insulating metallic oxide has said flange section protruding in the lateral direction, while said solid electrolyte has no flange.

8. The gas concentration detector in accordance with claim 1, wherein said sensor element has a two-cell structure comprising a pump cell and a sensor cell which are stacked.

9. The gas concentration detector in accordance with claim 8, wherein each of said pump cell and said sensor cell of said sensor element comprises a sensor section comprising a pair of electrodes provided on a plate solid electrolyte made of oxygen ion conductive metallic oxide, and said solid electrolyte is bonded on a substrate made of electrical insulating metallic oxide.

10. The gas concentration detector in accordance with claim 1, wherein said sensor element comprises a heater element.

11. The gas concentration detector in accordance with claim 1, wherein said plate sensor element has a polygonal cross section.

12. The gas concentration detector in accordance with claim 11, wherein said polygonal cross section of said plate sensor element is a quadrangular cross section.

13. The gas concentration detector in accordance with claim 1, wherein said flange section protrudes in parallel with a longer side of a cross section of said plate sensor element when said cross section is taken along a plane normal to said axis of said plate sensor element.

14. A gas concentration detector comprising:

a sensor element including a sensing section, a signal output section, and a flange section positioned between said sensing section and said signal output section;

said sensor element having at least one flush side face extending in a longitudinal direction of said sensor element from an end of said sensing section to an opposite end of said signal output section;

a cylindrical housing having an inside space for accommodating said sensor element; and powder filled in a predetermined space enclosed by at least an inside wall of said cylindrical housing and a flange surface adjacent to said signal output section, so that said sensor element is surrounded in an air tight fashion by said powder along an entire periphery thereof and fixed to said housing via said powder when a pressing force is applied on said powder, wherein a cross-sectional area of said signal output section is larger than a cross-sectional area of said sensing section when said cross-sectional areas are taken along a plane normal to the axis of said sensor element, said flange section is not provided on said flush side face of said sensor element, and said flange section is supported by said cylindrical housing with no intervening powder.

15. The gas concentration detector in accordance with claim 14, wherein said flange section has another flange surface adjacent to said sensing section, said another flange surface is held by said housing with no intervening powder.

16. The gas concentration detector in accordance with claim 14, wherein at least one electrode for detecting gas concentration is disposed on said flush side face of said sensor element.

17. The gas concentration detector in accordance with claim 14, wherein a signal lead for outputting a sensor signal is disposed along said flush side face of said sensor element.

18. A gas concentration detector comprising:

a rectangular sensor element having a rectangular cross section, including a sensing portion and a signal output portion;

opposite side faces of said rectangular sensor element being formed into flange portions located between said sensing portion and said output portion;

other opposite side faces of said rectangular sensor element being formed into parallel flush surfaces each extending in a longitudinal direction of said rectangular sensor element from an end of said sensing portion to an opposite end of said signal output portion;

a cylindrical housing having an inside space for accommodating said rectangular sensor element; and powder filled in a predetermined space enclosed by at least an inside wall of said cylindrical housing and flange surfaces adjacent to said signal output portion, so that said rectangular sensor element is surrounded in an air tight fashion by said powder along an entire periphery thereof and fixed to said cylindrical housing via said powder when a pressing force is applied on said powder, wherein a rectangular cross section of said signal output portion is larger than a rectangular cross section of said sensing portion when said cross sections are taken along a plane normal to the axis of said sensor element, said flange portions are not provided on said parallel flush surfaces of said rectangular sensor element, and said flange portions are supported by said cylindrical housing with no intervening powder.

19. The gas concentration detector in accordance with claim 18, wherein said flush surfaces correspond to longer sides of said rectangular cross section of said sensor element, while said flange surfaces correspond to shorter sides of said rectangular cross section of said sensor element.

* * * * *